United States Patent [19]

Reifschneider et al.

[11] Patent Number: 5,068,230
[45] Date of Patent: Nov. 26, 1991

[54] N-(((ALKOXY(ALKYLTHIO)PHOSPHINYL)AMINO)CARBONYL)-AMINOALKANOATE ESTER INSECTICIDES

[75] Inventors: Walter Reifschneider, Walnut Creek; Barat Bisabri-Ershadi, Davis; James E. Dripps, Concord; J. Brian Barron, Benicia, all of Calif.

[73] Assignee: The Dow Chemical Company, Midland, Mich.

[21] Appl. No.: 419,056

[22] Filed: Oct. 10, 1989

[51] Int. Cl.$^5$ ............... A01N 57/28; A01N 57/30
[52] U.S. Cl. ............... 514/115; 514/112; 546/22; 548/413; 558/139; 558/168; 558/171
[58] Field of Search ............... 558/168, 171; 514/112, 514/115

[56] References Cited

U.S. PATENT DOCUMENTS 4,259,330  3/1981  Aller et al. ............... 558/171

OTHER PUBLICATIONS

Derkach et al., *Zh. Obshch. Khim.*, 33, 1587–1591 (1963).
Samarai et al., *Zn. Obshch. Khim.*, 39, 1511–1513 (1969).
Derkach et al., *Zh. Obshch. Khim.*, 34, 3060–3063 (1964).
Mel'nikov et al., *Zh. Obshch. Khim.*, 47, 1711–1715 (1977) (Chemical Abstracts, 87, 183905n (1977)).
Alimov et al., *Isv. Akad. Nauk SSSR, Ser. Khim.*, 1964, 187–189 (Chemical Abstract, 60, 9144h (1964)).
Krikstiansen et al., Chemical Abstracts, vol. 89, No. 179559b, (1978).
Krikstiansen et al., Chemical Abstract, vol. 88, No. 70501e, (1977).

*Primary Examiner*—Mukund J. Shah
*Assistant Examiner*—Philip Datlow
*Attorney, Agent, or Firm*—D. Wendell Osborne

[57] ABSTRACT

Ester and amide derivatives of N-(((alkoxy-(alkylthio)-phosphinyl)amino)carbonyl)amino)alkanecarboxylic acids of the formula:

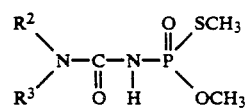

(wherein $R^2$ represents an alkyl group containing a carboxylic acid ester or amide moiety) were prepared by the reaction of O,S-dialkyl phosphoroisocyanatidothioates and ester and amide derivatives of naturally occurring and synthetic aminoacids and were found to be effective plant systemic and contact insecticides. Ethyl N-(((methoxy(methylthio)phosphinyl)amino)-carbonyl)methioninate, for example, were prepared from O,S-dimethyl phosphoroisocyanatidothioate and ethyl methioninate and found to control aster leafhoppers when applied to rice plants.

18 Claims, No Drawings

N-(((ALKOXY(ALKYLTHIO)PHOSPHINYL)AMINO)CARBONYL)-AMINOALKANOATE ESTER INSECTICIDES

BACKGROUND OF THE INVENTION

The present invention relates to N-(((alkoxy-(alkylthio)phosphinyl)amino)carbonyl)aminoalkanoic acid based compounds derived from naturally occurring and related aminoacids, to insecticidal compositions containing the compounds, and to the use of the compounds as insecticides.

The control of insects is critical to modern agriculture and to the maintenance of public health. Although many compounds that are useful in the control of insects are known, new compounds that are more effective, are less toxic to mammals, are more compatible with the environment, are less expensive, or have other outstanding properties are constantly sought and when found highly valued.

Many of the compounds known to be useful in the control of insects are organophosphorus compounds. Such compounds include O,S-dimethyl phosphoramidothioate (methamidophos) and O,S-dimethyl acetylphosphoramidothioate (acephate). Certain O,S-dialkyl N,N-dialkylcarbamoylphosphoramidothioates and their use as insecticides is disclosed in published German Patent Applications 2,718,554, and 2,805,682. The use of these known compounds as insecticides is often limited due to their toxicological and environmental properties, their lack of persistance, and their lack of activity on certain important insects. A ((((diethoxy)thiophosphinyl)amino)thiocarbonyl)glycinate ester has also been disclosed (Chemical Abstracts, 60, 9144H (1964)).

SUMMARY OF THE INVENTION

It has now been found that certain N-(((alkoxy-(alkylthio)phosphinyl)amino)carbonyl)aminoalkanoic acid based compounds, which can alternately be considered to be O,S-dialkyl N-(substituted-carbamoyl)phosphoramidothioates, have excellent plant systemic and contact insecticidal, acaracidal, and nematicidal activity against important species, but are relatively low in mammalian and fish toxicity.

The invention includes N-(((alkoxy(alkylthio)-phosphinyl)amino)carbonyl)aminoalkanoic acid based compounds of the formula

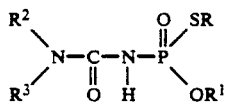

wherein
R and R$^1$ each independently represent C$_1$–C$_4$ alkyl;
R$^2$ represents —CH(R$^4$)—(CH$_2$)$_n$—A and R$^3$ represents H, C$_1$–C$_4$ alkyl or R$^2$ and R$^3$ taken together represent the fragment —(CH$_2$)$_p$—CH((CH$_2$)$_n$A)—(CH$_2$)$_q$—;
A represents CO$_2$R, CONR$^5$$_2$, or CN;
R$^4$ represents H, C$_1$–C$_4$ alkyl, —(CH$_2$)$_m$—A, —(CH$_2$)$_m$—SCH$_3$, or —C$_6$H$_5$;
each R$^5$ independently represents H or C$_1$–C$_4$ alkyl;
m represents 1 or 2;
n represents 0, 1, or 2; and
p and q each independently represent 0, 1, 2, 3 or 4 with the proviso that the sum of p and q represents 3 or 4.

Compositions containing insecticidal amounts of the compounds of the invention in admixture with at least one agriculturally acceptable adjuvant or carrier are useful for the control of insects. A wide variety of insects is controlled by application of insecticidal amounts of the compounds to the insects or to their locus or to plants that insects feed on or their locus. Both plant systemic and contact insecticidal activity are exhibited. Sucking insects, such as leafhoppers, are especially susceptible.

DETAILED DESCRIPTION OF THE INVENTION

The compounds of the present invention include those N-(((alkoxy(alkylthio)phosphinyl)amino)carbonyl)-aminoalkanoic acid based compounds of the formula

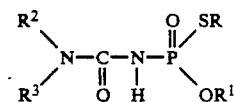

wherein
R and R$^1$ each independently represent C$_1$–C$_4$ alkyl;
R$^2$ represents —CH(R$^4$)—(CH$_2$)$_n$—A and R$^3$ represents H, C$_1$–C$_4$ alkyl or R$^2$ and R$^3$ taken together represent the fragment —(CH$_2$)$_p$—CH((CH$_2$)$_n$A)—(CH$_2$)$_1$—;
A represents CO$_2$R, CONR$^5$$_2$, or CN;
R$^4$ represents H, C$_1$–C$_4$ alkyl, —(CH$_2$)$_m$—A, —(CH$_2$)$_m$—SCH$_3$, or —CH$_2$C$_6$H$_5$;
each R$^5$ independently represents H or C$_1$–C$_4$ alkyl;
m represents 1 or 2;
n represents 0, 1, or 2; and
p and q each independently represent 0, 1, 2, 3 or 4 with the proviso that the sum of p and q represents 3 or 4.

The compounds of the invention can be characterized as substituted O,S-dialkyl N-(substituted-carbamoyl)-phosphoramidothioate esters in which the substituted-carbamoyl moiety is derived from a naturally occurring or synthetic aminoacid. Compounds derived from the lower alkyl esters, amides, lower alkyl amides, and nitriles obtained by modifying the acid function of aminoacids, such as glycine, N-methylglycine (sarcosine), L-alanine, DL-phenylalanine, methionine, proline, 4-aminobutyric acid, and 2-, 3-, or 4-piperidinecarboxylic acids are typical. Such derivatives of glycine, sarcosine, alanine methionine proline, piperidine-3-carboxylic acid, and piperidine-4-carboxylic acid are often preferred. Compounds of the formula given above wherein A represents (C$_1$–C$_4$ alkoxy)carbonyl or unsubstituted carbamoyl; i.e., C$_1$–C$_4$ esters or unsubstituted amide derivatives, are also often preferred. Compounds in which the number n represents zero are often preferred.

The R and R$^1$ substituents on the phosphorothioic acid moiety of the compounds of the invention are independently selected from either straight chain or branched chain C$_1$–C$_4$ alkyl groups. Methyl, ethyl, propyl, isopropyl, and isobutyl are typical. Compounds wherein both R and R$^1$ represent methyl are often preferred as are compounds wherein R represents n-propyl and $R^1$ represents ethyl.

The compounds of the present invention contain an asymmetric phosphorus atom and in most cases one or more asymmetric carbon atoms and, therefore, exist as optical isomers. The present invention relates to each of these optical isomers individually and to all mixtures thereof as well as to all geometric isomers. Aminoacids from natural sources usually have the L configuration.

The compounds of the invention include, but are not limited by, the compounds illustrated in the following table.

$$\begin{array}{c} R^2 \\ \diagdown \\ R^3 \end{array} N - \underset{\underset{O}{\|}}{C} - \underset{H}{N} - \underset{\underset{OR^1}{|}}{\overset{\overset{O}{\|}}{P}} \diagdown SR$$

| Cpd. No. | R | $R^1$ | $R^2N(R^3)-$ | MP, °C. or RI@25° C. | Elem. Anal. 1 |
|---|---|---|---|---|---|
| 1 | $CH_3$ | $CH_3$ | $CH_3O_2C-CH_2NH-$ | 133–135 | CHN |
| 2 | $CH_3$ | $CH_3$ | $C_2H_5O_2C-CH_2NH-$ | 143–145 | CHN |
| 3 | $CH_3$ | $CH_3$ | (DL)$C_2H_5O_2C-\underset{\underset{CH_3}{\|}}{C}HNH-$ | 103–106 | CHN |
| 4 | $CH_3$ | $CH_3$ | (L)$C_2H_5O_2C-\underset{\underset{CH_3}{\|}}{C}HNH-$ | 130–132 | CHN |
| 5 | $CH_3$ | $CH_3$ | (DL)$C_2H_5O_2C-\underset{\underset{CH_3SCH_2CH_2}{\|}}{C}HNH-$ | 108–110 | CHN |
| 6 | $CH_3$ | $CH_3$ | (DL)$C_2H_5O_2C-\underset{\underset{C_6H_5CH_2}{\|}}{C}HNH-$ | 148–150 | CHN |
| 7 | $CH_3$ | $CH_3$ | (DL)$C_2H_5O_2C-\underset{\underset{C_2H_5O_2C-CH_2}{\|}}{C}HNH-$ | 115–116 | CHN |
| 8 | $CH_3$ | $CH_3$ | (DL)$C_2H_5O_2C-\underset{\underset{C_2H_5O_2C-CH_2CH_2}{\|}}{C}HNH-$ | 114–115 | CHN |
| 9 | $CH_3$ | $CH_3$ | $CH_3O_2C-CH_2CH_2NH-$ | 143–145 | CHN |
| 10 | $CH_3$ | $CH_3$ | $CH_3O_2C-CH_2CH_2CH_2NH-$ | 99–101 | CHN |
| 11 | $CH_3$ | $CH_3$ | $C_2H_5O_2C-CH_2N(CH_3)-$ | 1.5052 | CHN |
| 12 | $CH_3$ | $CH_3$ | $i\text{-}C_3H_7O_2C-CH_2N(CH_3)-$ | 1.4964 | CHN |
| 13 | $C_3H_7$ | $C_2H_5$ | $C_2H_5O_2C-CH_2N(CH_3)-$ | 1.4957 | CHN |
| 14 | $CH_3$ | $CH_3$ | (DL)$C_2H_5O_2C-\underset{\underset{CH_3}{\|}}{C}HN(CH_3)-$ | 1.5056 | CHN |
| 15 | $CH_3$ | $CH_3$ | (DL)C2H5O2C-CH-N(CH2CH2CH2) ring | 1.5168 | CHN |
| 16 | $CH_3$ | $CH_3$ | $H_2NCO-CH_2NH-$ | 165–166 | CHN |
| 17 | $CH_3$ | $CH_3$ | $H_2NCO-CH_2N(CH_3)-$ | 126–127 | CHN |
| 18 | $CH_3$ | $CH_3$ | $NC-CH_2N(CH_3)-$ | 106–107 | CHN |
| 19 | $CH_3$ | $CH_3$ | $(NC-CH_2)_2N-$ | 99–101 | CHN |
| 20 | $CH_3$ | $CH_3$ | pyrrolidine-CH($CO_2C_2H_5$)-N- | 1.5139 | CHN |
| 21 | $CH_3$ | $CH_3$ | piperidine-CH($CH_3O_2C$)-N- | 65–67 | CHN |

-continued $$\begin{array}{c} R^2 \\ \diagdown \\ R^3 \end{array} N-C-N-P \begin{array}{c} O \\ \parallel \\ H \end{array} \begin{array}{c} SR \\ \diagup \\ OR^1 \end{array}$$

| Cpd. No. | R | $R^1$ | $R^2N(R^3)-$ | MP, °C. or RI@25° C. | Elem. Anal. 1 |
|---|---|---|---|---|---|
| 22 | $CH_3$ | $CH_3$ | $C_2H_5O_2C$-CH—CH$_2$ / CH$_2$ / CH$_2$—CH$_2$ N— | 1.5169 | CHN |
| 23 | $CH_3$ | $CH_3$ | $H_2N(O)C$-CH—CH$_2$ / CH$_2$ / CH$_2$—CH$_2$ N— | 132–135 | CHN |
| 24 | $CH_3$ | $CH_3$ | $C_2H_5O_2C$—CH$_2$-CH—CH$_2$ / CH$_2$ / CH$_2$—CH$_2$ N— | 103–105 | CHN |
| 25 | $CH_3$ | $CH_3$ | $C_2H_5O_2C$—CH, CH$_2$—CH$_2$ / CH$_2$—CH$_2$ N— | 1.5173 | |
| 26 | $C_3H_7$ | $C_2H_5$ | $CO_2C_2H_5$ / CH$_2$—CH / CH$_2$ / CH$_2$—CH$_2$ N— | 1.5043 | CHN |
| 27 | $C_3H_7$ | $C_2H_5$ | $CH_3O_2C$-CH—CH$_2$ / CH$_2$ / CH$_2$—CH$_2$ N— | 1.5117 | CHN |
| 28 | $C_3H_7$ | $C_2H_5$ | $C_2H_5O_2C$—CH$_2$-CH—CH$_2$ / CH$_2$ / CH$_2$—CH$_2$ N— | 1.5064 | CHN |
| 29 | $C_3H_7$ | $C_2H_5$ | $C_2H_5O_2C$—CH, CH$_2$—CH$_2$ / CH$_2$—CH$_2$ N— | 1.5083 | CHN |

1 Acceptable analyses obtained

The compounds of the present invention can be prepared by the reaction of an appropriate O,S-dialkyl phosphoroisocyanatidothioate and an appropriate aminoacid derivative as shown in the following scheme wherein all substituents are defined as above:

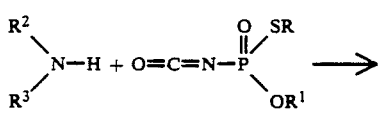

$$\begin{array}{c} R^2 \\ \diagdown \\ R^3 \end{array} N-C-N-P \begin{array}{c} O \\ \parallel \\ H \end{array} \begin{array}{c} SR \\ \diagup \\ OR^1 \end{array}$$

The reaction can be conducted by combining the two starting materials in a solvent, such as ether, methylene chloride, or acetonitrile at about −10° C. to about 60° C. and allowing them to react. The product, a compound of the present invention, that forms can be recovered by conventional means, such as by evaporation of the solvent or, in the case of solids, by filtration and drying. The recovered products can be purified by conventional means, such as by liquid chromatography, by extraction with solvents in which the products are poorly soluble, or, in the case of solids, by recrystallization. The compounds of the invention are generally oily liquids or relatively low melting solids.

The starting materials for the above method are well known in the art or can readily be prepared using the methods taught in the art. The preparation of the isocyanatidophosphoramidate esters can be conveniently accomplished by heating an O,S-dialkyl phosphoramidothioate with phosgene or oxalyl chloride in a solvent. The preparation of the starting material aminoacids varies with the structure but is well established in the art as is the modification of the acid function of aminoacids.

The compounds of the present invention can be used directly as insecticides, but it is generally preferable to first prepare an insecticidal composition containing one or more of the compounds in combination with an agriculturally acceptable adjuvant or carrier. Suitable adjuvants or carriers should not be phytotoxic to valuable crops, particularly at the concentrations employed in applying the compositions for insect control in the presence of crops, and should not react chemically with the insecticidal compounds or other composition ingredients. Such mixtures can be designed for application directly to plants or their locus or can be concentrates or formulations which are normally diluted with additional carriers and adjuvants before application. They can be solids, such as, for example, dusts, granules, water dispersible granules, or wettable powders, or liquids, such as, for example, emulsifiable concentrates, solutions, emulsions or suspensions.

Suitable agricultural adjuvants and carriers that are useful in preparing the insecticidal mixtures of the invention are well known to those skilled in the art.

Liquid carriers that can be employed include water, toluene, xylene, petroleum naphtha, crop oil, acetone, methyl ethyl ketone, cyclohexanone, trichloroethylene, perchloroethylene, ethyl acetate, amyl acetate, butyl acetate, propylene glycol monomethyl ether and diethylene glycol monomethyl ether, isopropyl alcohol, amyl alcohol, ethylene glycol, propylene glycol, glycerine, and the like. Water is generally the carrier of choice for the dilution of concentrates.

Suitable solid carriers include talc, pyrophyllite clay, silica, attapulgus clay, kieselguhr, chalk, diatomaceous earth, lime, calcium carbonate, bentonite clay, Fuller's earth, cotton seed hulls, wheat flour, soybean flour, pumice, wood flour, walnut shell flour, lignin, and the like.

It is frequently desirable to incorporate one or more surface-active agents into the compositions of the present invention. Such surface-active agents are advantageously employed in both solid and liquid compositions, especially those designed to be diluted with carrier before application. The surface-active agents can be anionic, cationic or nonionic in character and can be employed as emulsifying agents, wetting agents, suspending agents, or for other purposes. Typical surface active agents include salts of alkyl sulfates, such as diethanolammonium lauryl sulfate; alkylarylsulfonate salts, such as calcium dodecylbenzenesulfonate: alkylphenolalkylene oxide addition products, such as nonylphenol-$C_{18}$ ethoxylate: alcohol-alkylene oxide addition products, such as tridecyl alcohol-$C_{16}$ ethoxylate: soaps, such as sodium stearate; alkylnaphthalenesulfonate salts, such as sodium dibutylnaphthalenesulfonate: dialkyl esters of sulfosuccinate salts, such as sodium di(2-ethylhexyl) sulfosuccinate: sorbitol esters, such as sorbitol oleate; quaternary amines, such as lauryl trimethylammonium chloride: polyethylene glycol esters of fatty acids, such as polyethylene glycol stearate: block copolymers of ethylene oxide and propylene oxide: and salts of mono and dialkyl phosphate esters.

Other adjuvants commonly utilized in agricultural compositions include antifoam agents, compatibilizing agents, sequestering agents, neutralizing agents and buffers, corrosion inhibitors, dyes, odorant, penetration aids, spreading agents, sticking agents, dispersing agents, thickening agents, freeze point depressants, antimicrobial agents, and the like. The compositions can also contain other compatible components, for example, fungicides, other insecticides, and the like and can be formulated with solid, particulate fertilizer carriers such as ammonium nitrate, urea and the like or with liquid fertilizers.

The concentration of the active ingredients in the insecticidal compositions of this invention is generally from about 0.001 to about 98 percent by weight. Concentrations from about 0.01 to about 90 percent by weight are often employed. In compositions designed to be employed as concentrates, the active ingredient is generally present in a concentration from about 5 to about 98 weight percent, preferably about 10 to about 90 weight percent. Such compositions are typically diluted with an inert carrier, such as water, before application. The diluted compositions usually applied to insects or their locus or to plants or their locus generally contain about 0.001 to about 0.1 weight percent active ingredient and preferably contain about 0.005 to about 0.05 percent.

The present compositions can be applied by the use of conventional ground or aerial dusters and sprayers, by addition to irrigation water, and by other conventional means known to those skilled in the art.

The compounds of the invention are useful for the control of a wide variety of insects, mites, and nematodes. Sucking and chewing insects, especially sucking insects, are susceptible to the compounds. Leafhoppers, in particular, are well controlled.

The compounds are active against insect pests by both contact and plant systemic action and, consequently, can be applied either directly to the insects or to the locus thereof so that they will come in contact with the exterior parts of the insect pest or can be applied to plants insects feed on or the locus of such plants so that they will be ingested by the insect pests. It is often preferred to apply the compounds to plants or to the locus of plants and take advantage of the plant systemic properties of the compounds. The treatment of rice plants or their locus to control leaf hoppers is a preferred application.

The following examples are presented to illustrate the invention: they should not be construed as limiting.

EXAMPLES

Example 1—Preparation of Ethyl N-(((Methoxy-(methylthio)phosphinyl)amino)carbonyl)glycinate To a solution of 6.1 grams (g) of O,S-dimethyl phosphoroisocyanatidothioate in 100 milliliters (ml) of ether was added dropwise with stirring 3.5 g of ethyl glycinate. A solid soon began to precipitate and after about 1 hour this was collected by filtration. The solid was recrystallized from ethanol to obtain 7.4 g of the title compound (77 percent of theory) as white crystals melting at 143°-145° C.

Elemental Analysis (Percent):
Calc for $C_7H_{15}N_2O_5PS$: C, 31.11: H, 5.59: N, 10.37
Found C, 31.07; H, 5.61: N, 10.39

Example 2—Preparation of Ethyl N-(((Ethoxy-(propylthio)phosphinyl)amino)carbonyl)-N-methylglycinate To a solution of 3.4 g of 0-ethyl S-n-propyl phosphoroisocyanatidothioate in 30 ml of ether was added dropwise with stirring 2.0 g of ethyl sarcosinate. The mixture was stirred for 2 hours at ambient temperature and was then concentrated by evaporation under reduced pressure on a rotary evaporator to obtain 5.3 g (98 percent of theory) of the title compound as a pale yellow oil having a refractive index at 25° C. of 1.4957.

Elemental Analysis (Percent):
Calc for $C_{11}H_{23}N_2O_5PS$: C, 40.48: H, 7.10: N, 8.59
Found C, 39.94: H, 7.09: N, 8.41

Example 3—Preparation of Methyl 1-(((Methoxy-(methylthio)phosphinyl)amino)carbonyl-3-piperidinecarboxylate A solution of 8.36 g of O,S-dimethyl phosphoroisocyanatidothioate in 100 ml of ether was cooled to 0° C. and to it was added dropwise with stirring 7.15 g of methyl 3-piperidinecarboxylate. The mixture was allowed to warm to ambient temperature and react overnight. The precipitate that formed was collected by filtration, extracted with ether, and dried under reduced pressure to obtain 11.5 g (74 percent of theory) of the title compound as white crystals melting at 65°-67° C.

Elemental Analysis (Percent):
Calc for $C_{10}H_{19}N_2O_5PS$: C, 38.70; H, 6.17; N, 9.03
Found C, 38.83; H, 6.13: N, 8.94

Example 4—Preparation of Ethyl 1-(((Ethoxy-(propylthio)phosphinyl)amino)carbonyl)-4-piperidinecarboxylate To a solution of 2.36 g of ethyl 4-piperidinecarboxylate in 50 ml of ether at ambient temperature was added dropwise with stirring 3.14 g of 0-ethyl S-n-propyl phosphoroisocyanatidothioate. The mixture was allowed to stir overnight and was then concentrated by evaporation under reduced pressure using a rotary evaporator and then a Kugelrohr apparatus at 55° C. and 13 Pascals pressure. The residue, which was the title compound, amounted to 5.2 g (94 percent of theory) and was an amber colored viscous oil having a refractive index at 25° C. of 1.5083.

Elemental Analysis (Percent):
Calc for $C_{14}H_{27}N_2O_5PS$: C, 45.89: H, 7.43; N, 7.65
Found C, 45.58: H, 7.48: N, 7.45

Example 5—Insecticidal Activity Against Aster LeafHopper

Test compounds were dissolved in a small amount of acetone and the resulting solutions were diluted with distilled water containing 0.1 percent Triton ™ X-100 surfactant (an octylphenol ethoxylate nonionic surfactant) to obtain application mixtures containing known amounts. Rice plants were grown in vermiculite in a greenhouse under controlled conditions.

Foliar treatments were made to determine the contact insecticidal activity. Individual rice plants were sprayed to runoff with an application mixture containing a known concentration of a test compound and then the plants were allowed to dry for 1 hour. Control plants were treated in the same way with a surfactant solution prepared in the same way as the application mixtures. Root treatments were made to determine the systemic insecticidal activity. Individual rice plants were transferred to an individual hydroponic system and 25 ml of an application mixture containing a known concentration of a test compound was added to the system. Control plants were treated in the same way with a surfactant solution prepared in the same way as the application mixtures.

A plastic cylinder was placed around each of the plants and 10 adult aster leafhoppers (*Macrosteles severni*) were placed in each cylinder. The cylinders were capped and maintained under conditions conducive to the growth of the plants and the insects. After two days the contents of each cylinder was examined to determine the percentage of the aster leafhoppers that were dead. The results were collected and an $LC_{50}$ (the concentration at which one half of the insects died) calculated for each compound tested. The results are given in the following table.

| CONTROL OF ASTER LEAFHOPPERS | | |
|---|---|---|
| Compound Number | Contact $LC_{50}$, ppm | Systemic $LC_{50}$, ppm |
| 3 | 11 | 1.7 |
| 4 | 7 | 0.8 |
| 5 | 14 | 2.0 |
| 7 | >20 | 5.0 |
| 8 | 18 | 3.1 |
| 10 | >20 | >5.0 |
| 11 | 27 | 3.2 |
| 12 | 17 | 1.2 |
| 13 | >40 | 2.3 |
| 14 | >40 | 3.9 |
| 15 | >20 | 1.7 |
| 16 | >10 | >2.5 |
| 17 | 36 | 3.2 |
| 18 | 28 | 4.8 |
| 20 | >20 | 2.7 |
| 21 | 13 | 1.7 |
| 22 | >20 | 1.4 |
| 23 | 12 | 0.7 |
| 24 | 20 | 2.7 |
| 25 | 8 | 0.6 |
| 26 | >20 | 2.6 |
| 27 | >20 | 5.0 |
| 28 | >20 | 4.2 |
| 29 | >20 | 2.4 |

What is claimed is:
1. A compound of the formula

$$\begin{array}{c} R^2 \\ \diagdown \\ R^3 \diagup \end{array} N-C-N-P \begin{array}{c} O \\ \| \\ \diagup \\ \diagdown \end{array} \begin{array}{c} SCH_3 \\ \\ OCH_3 \end{array}$$

wherein
R represents $C_1$-$C_4$ alkyl;
$R^2$ represents —CH($R^4$)—$(CH_2)_n$—A and $R^3$ represents H or $C_1$-$C_4$ alkyl;
A represents $CO_2R$ or $CONR^5{}_2$;
$R^4$ represents H, $C_1$-$C_4$ alkyl, —$(CH_2)_m$—A, —$(CH_2)_m$—$SCH_3$, or —$C_6H_5$;
each $R^5$ independently represents H or $C_1$-$C_4$ alkyl;

m represents 1 or 2; and n represents 0, 1, or 2.

2. A compound of claim 1 wherein n represents zero.

3. A compound of claim 1 wherein $R^3$ represents hydrogen or methyl.

4. A compound of claim 1, ethyl N-(((methoxy-(methylthio)phosphinyl)amino)carbonyl)methioninate.

5. A compound of claim 1, ethyl 1-(((methoxy-(methylthio)phosphinyl)amino)carbonyl)alaninate.

6. An insecticidal composition comprising an agriculturally acceptable adjuvant or carrier and an insecticidally effective amount of a compound of the formula

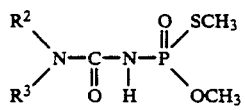

wherein

R represents $C_1$-$C_4$ alkyl;

$R^2$ represents —CH($R^4$)—($CH_2$)$_n$—A and $R^3$ represents H or $C_1$-$C_4$ alkyl;

A represents $CO_2R$ or $CONR^5$ $_2$;

$R^4$ represents H, $C_1$-$C_4$ alkyl, —($CH_2$)$_m$—A, —($CH_2$)$_m$—$SCH_3$, or —$C_6H_5$;

each $R^5$ independently represents H or $C_1$-$C_4$ alkyl;

m represents 1 or 2; and n represents 0, 1, or 2.

7. A composition of claim 6 wherein n represents zero.

8. A composition of claim 6 wherein $R^3$ represents hydrogen or methyl.

9. A composition of claim 6 containing the compound ethyl N-(((methoxy(methylthio)-phosphinyl)amino)carbonyl)methioninate.

10. A composition of claim 6 containing the compound ethyl N-(((methoxy(methylthio)phosphinyl)amino)carbonyl)alaninate.

11. A method of controlling insects which comprises contacting the insects or the locus thereof or the plants on which the insects feed or the locus thereof with an insecticidally effective amount of a compound of the formula

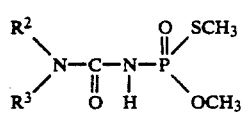

wherein

R represents $C_1$-$C_4$ alkyl;

$R^2$ represents —CH($R^4$)—($CH_2$)$_n$—A and $R^3$ represents H or $C_1$-$C_4$ alkyl;

A represents $CO_2R$ or $CONR^5$ $_2$;

$R^4$ represents H, $C_1$-$C_4$ alkyl, —($CH_2$)$_m$—A, —($CH_2$)$_m$—$SCH_3$, or —$C_6H_5$;

each $R^5$ independently represents H or $C_1$-$C_4$ alkyl;

m represents 1 or 2; and n represents 0, 1, or 2.

12. A method of claim 11 wherein n represents zero.

13. A method of claim 11 wherein $R^3$ represents hydrogen or methyl.

14. A method of claim 11 wherein the compound is ethyl N-(((methoxy(methylthio)-phosphinyl)amino)carbonyl)methioninate.

15. A method of claim 11 wherein the compound is ethyl N-(((methoxy(methylthio)phosphinyl)amino)-carbonyl)alaninate.

16. A method of claim 11 wherein the insects controlled are sucking insects.

17. A method of claim 16 wherein the insects are leafhoppers.

18. A method of claim 11 wherein the plants are rice plants.

* * * * *